US012569372B2

(12) United States Patent (10) Patent No.: US 12,569,372 B2
Quincy, III et al. (45) Date of Patent: Mar. 10, 2026

(54) ABSORBENT ARTICLE WITH FLUID CONTROL FEATURES

(71) Applicant: Kimberly-Clark Worldwide, Inc., Neenah, WI (US)

(72) Inventors: Roger Bradshaw Quincy, III, Roswell, GA (US); Kerry Lynn Clemmer, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 18/870,961

(22) PCT Filed: Nov. 10, 2023

(86) PCT No.: PCT/US2023/037127
§ 371 (c)(1),
(2) Date: Dec. 2, 2024

(87) PCT Pub. No.: WO2025/101179
PCT Pub. Date: May 15, 2025

(65) Prior Publication Data
US 2025/0177214 A1 Jun. 5, 2025

(51) Int. Cl.
*A61F 13/15* (2006.01)
*A61F 13/53* (2006.01)
*A61F 13/537* (2006.01)

(52) U.S. Cl.
CPC .. *A61F 13/15203* (2013.01); *A61F 13/53756* (2013.01); *A61F 13/5376* (2013.01); *A61F 2013/15406* (2013.01); *A61F 2013/15552*

(2013.01); *A61F 2013/530007* (2013.01); *A61F 2013/530167* (2013.01); *A61F 2013/530299* (2013.01)

(58) Field of Classification Search
CPC ........ A61F 13/511; A61F 13/51; A61F 13/53; A61F 2013/15552; A61F 2013/530299; A61F 13/15203; A61F 13/53756; A61F 13/5376; A61F 2013/15406; A61F 2013/530007; A61F 2013/530167; A61F 13/53747; A61F 2013/530496
See application file for complete search history.

(56) References Cited

U.S. PATENT DOCUMENTS 3,338,992 A 8/1967 Allison
3,341,394 A 9/1967 Allison
(Continued)

FOREIGN PATENT DOCUMENTS

CA 2143791 * 4/1996 ............. A61F 13/46
CN 108291346 B 5/2021
(Continued)

OTHER PUBLICATIONS

PCT Search Report Corresponding to Application No. PCT/US2023/037127 on Aug. 9, 2024.

*Primary Examiner* — Michele Kidwell
(74) *Attorney, Agent, or Firm* — Dority & Manning, P.A.

(57) ABSTRACT
An absorbent article includes a bodyside liner, an absorbent core, and an acquisition layer positioned between the bodyside liner and the absorbent core. Properties of the bodyside liner, absorbent core, and acquisition layer may facilitate fluid flow within a target zone and provide the absorbent article with desired dryness.

20 Claims, 2 Drawing Sheets

(56) References Cited

U.S. PATENT DOCUMENTS

| | | | |
|---|---|---|---|
| 3,502,538 A | | 3/1970 | Petersen |
| 3,502,763 A | | 3/1970 | Hartmann |
| 3,542,615 A | | 11/1970 | Dobo et al. |
| 3,692,618 A | | 9/1972 | Dorschner et al. |
| 3,802,817 A | | 4/1974 | Matsuki et al. |
| 3,849,241 A | | 11/1974 | Butin et al. |
| 4,340,563 A | | 7/1982 | Appel et al. |
| 4,601,868 A | * | 7/1986 | Radel ................ A61F 13/51104 |
| | | | 425/290 |
| 5,628,097 A | * | 5/1997 | Benson ..................... B26F 1/00 |
| | | | 28/165 |
| 8,791,321 B2 | | 7/2014 | Love et al. |
| 2013/0231622 A1 | * | 9/2013 | Dieringer .......... A61F 13/51108 |
| | | | 604/374 |
| 2019/0021913 A1 | * | 1/2019 | Wang ................ A61F 13/15203 |
| 2020/0054782 A1 | | 2/2020 | Chan et al. |
| 2021/0000655 A1 | * | 1/2021 | Martynus .......... A61F 13/15203 |
| 2021/0022931 A1 | * | 1/2021 | Chan ................ A61F 13/15203 |
| 2021/0085536 A1 | | 3/2021 | Isaac |

FOREIGN PATENT DOCUMENTS

| | | | | |
|---|---|---|---|---|
| EP | 3209259 | * | 3/2023 | ........... A61F 13/512 |
| WO | WO2002076520 A2 | | 10/2002 | |
| WO | WO2023274892 A1 | | 1/2023 | |

* cited by examiner

ABSORBENT ARTICLE WITH FLUID CONTROL FEATURES

RELATED APPLICATIONS

The present application is the national stage entry of International Patent Application No. PCT/US2023/037127 having a filing date of Nov. 10, 2023, which is incorporated herein in its entirety by reference thereto.

BACKGROUND

Personal care absorbent articles, such as diapers and incontinence briefs, frequently include various layers and an absorbent core that rapidly absorbs bodily fluids (e.g., urine) and traps the fluids therein to limit re-transmission of the fluids to the wearer. The absorbent core can include pulp fluff and superabsorbent material for absorbing the fluids.

Characteristics of the personal care absorbent articles can affect consumer perception of the personal care absorbent articles. For example, rapidly moving fluids away from the wearer and retaining the fluids away from the wearer can keep the wearer's skin dry. Maintaining dryness is an important characteristic for personal care absorbent articles. However, known absorbent articles can have limitations with respect to dryness.

An absorbent article with features for controlling fluid flow to provide improved dryness would be useful.

SUMMARY

In general, the present disclosure is directed to an absorbent article with features for fluid control, e.g., to provide desired dryness. The absorbent article may have a target zone, which corresponds to a portion of the absorbent article expected to receive fluid intake. At the target zone, the absorbent article may include a bodyside liner, an acquisition layer, and an absorbent core. The acquisition layer may be positioned below the bodyside liner, and the absorbent core may be positioned below the acquisition layer. Lengths of the bodyside liner and the absorbent core may extend along a longitudinal direction and be about equal to the length of the absorbent article. The length of the acquisition layer may be less than the lengths of the bodyside liner and the absorbent core. For instance, the length of the acquisition layer may be about equal to the length of the target zone. In example embodiments, fluid in the absorbent article may be controlled such that the fluid does not extend beyond the acquisition layer.

The properties of the bodyside liner, the acquisition layer, and the absorbent core may be selected to facilitate dryness, e.g., such that a second rewet of the absorbent article is less than three-tenths of a gram (0.3 g) according to a Rewet Test. For instance, the bodyside liner may be configured such that an air permeability of the bodyside liner is no less than thirteen thousand cubic meters per hour per square meter surface (13,000 $m^3ph/m^2$) and no greater than sixteen thousand, five hundred cubic meters per hour per square meter surface (16,500 $m^3ph/m^2$). Moreover, the bodyside liner may be treated with a surfactant to provide a desired degree of wettability and hydrophilicity. The acquisition layer may have an air permeability no less than twelve thousand, seven hundred cubic meters per hour per square meter surface (12,700 $m^3ph/m^2$). The absorbent core may also include superabsorbent material at no less than fifty percent (50%) by weight of a matrix of cellulosic fluff and superabsorbent material. Such properties may advantageously maintain fluid within the target zone and avoid flow of the fluid outside the target zone, where the fluid is less likely to be maintained within the absorbent core. Such properties may advantageously provide the absorbent article with desired dryness, e.g., without requiring increasing the size of the acquisition layer to match the bodyside liner and the absorbent core.

In one example embodiment, an absorbent article includes a bodyside liner having an air permeability no less than thirteen thousand cubic meters per hour per square meter surface (13,000 $m^3ph/m^2$) and no greater than sixteen thousand, five hundred cubic meters per hour per square meter surface (16,500 $m^3ph/m^2$). An absorbent core includes a matrix of cellulosic fluff and superabsorbent material. The superabsorbent material is present in the matrix at no less than fifty percent (50%) by weight of the matrix and no greater than eighty percent (80%) by weight of the matrix. An acquisition layer is positioned between the bodyside liner and the absorbent core. The acquisition layer has an air permeability no less than twelve thousand, seven hundred cubic meters per hour per square meter surface (12,700 $m^3ph/m^2$).

In another example embodiment, an absorbent article includes a bodyside liner having an air permeability no less than thirteen thousand cubic meters per hour per square meter surface (13,000 $m^3ph/m^2$) and no greater than sixteen thousand, five hundred cubic meters per hour per square meter surface (16,500 $m^3ph/m^2$). A basis weight of the bodyside liner may be no less than ten grams per square meter (10 gsm) and no greater than twenty grams per square meter (20 gsm). An absorbent core includes a matrix of cellulosic fluff and superabsorbent material. The superabsorbent material is present in the matrix at no less than fifty percent (50%) by weight of the matrix and no greater than eighty percent (80%) by weight of the matrix. An acquisition layer is positioned between the bodyside liner and the absorbent core. The acquisition layer has an air permeability no less than twelve thousand, seven hundred cubic meters per hour per square meter surface (12,700 $m^3ph/m^2$). A basis weight of the acquisition layer is no less than sixty grams per square meter (60 gsm) and no greater than one hundred grams per square meter (100 gsm).

These and other features, aspects and advantages of the present disclosure will become better understood with reference to the following description and appended claims. The accompanying drawings, which are incorporated in and constitute a part of this specification, illustrate embodiments of the disclosure and, together with the description, serve to explain the principles of the disclosure.

BRIEF DESCRIPTION OF THE DRAWINGS

A full and enabling disclosure of the present disclosure, including the best mode thereof, directed to one of ordinary skill in the art, is set forth in the specification, which makes reference to the appended figures.

Figure 1:
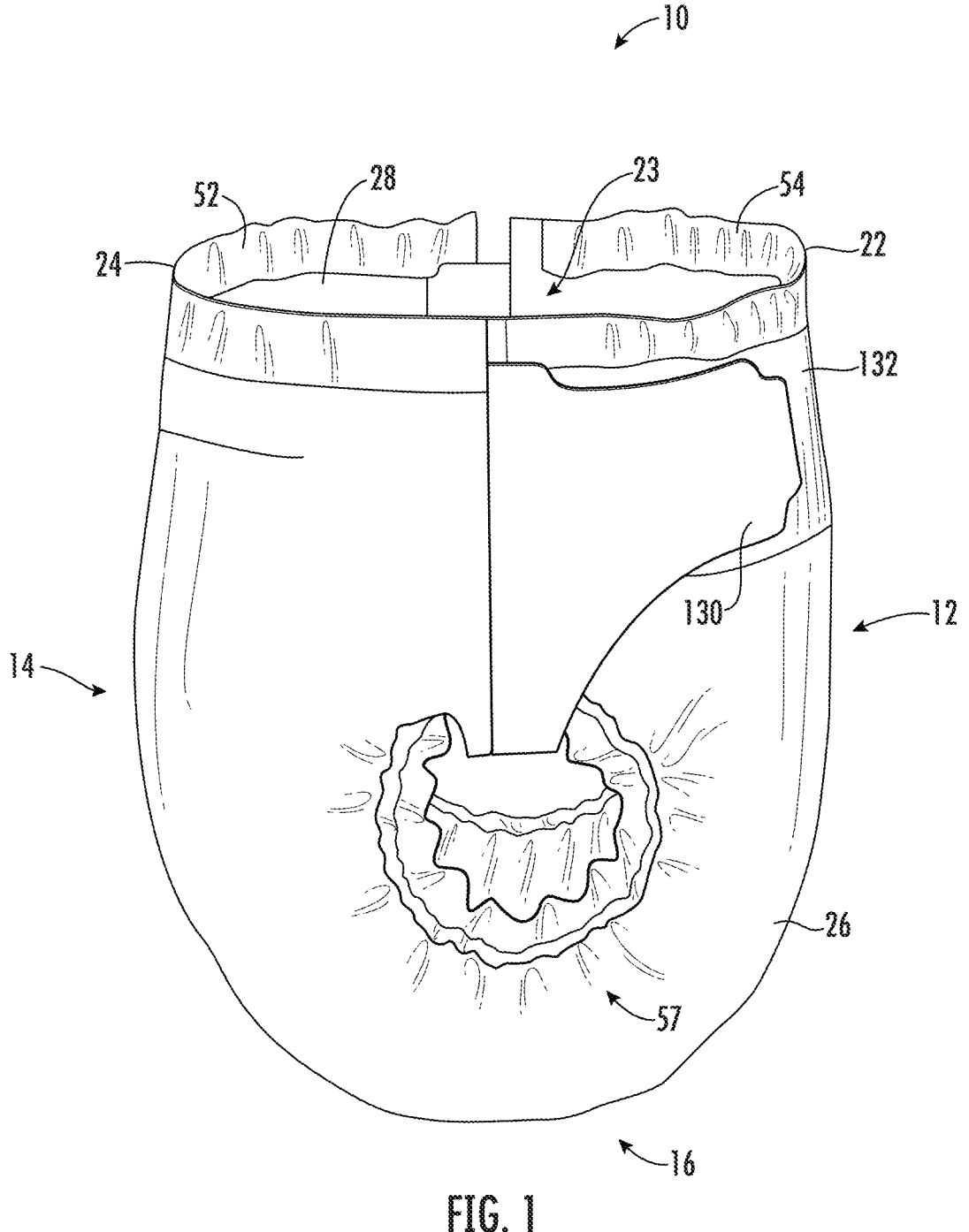
FIG. 1 is a side perspective view of an absorbent article, such as a diaper, according to example aspects of the present disclosure, in a fastened condition.

Repeat use of reference characters in the present specification and drawings is intended to represent the same or analogous features or elements of the present invention.

DETAILED DESCRIPTION

The present disclosure is generally directed to absorbent articles with features for fluid control, e.g., to provide desired dryness as indicated by a rewet value. The absorbent article may include a bodyside liner, an acquisition layer, and an absorbent body. The acquisition layer may be positioned between the bodyside liner and the absorbent body, e.g., at a target zone where repeated liquid surges typically occur in the absorbent article. For instance, the acquisition layer may be embossed to the bodyside liner. The acquisition layer may receive and temporarily hold liquid body exudates that pass through the bodyside liner, and the acquisition layer may decelerate and diffuse a surge or gush of the liquid body exudates as the liquid body exudates are absorbed by the absorbent body.

The bodyside liner, acquisition layer, and absorbent body may have various advantageous properties to facilitate fluid flow within the target zone. For instance, the bodyside liner may be configured such that an air permeability of the bodyside liner is no less than thirteen thousand cubic meters per hour per square meter surface (13,000 m³ph/m²) and no greater than sixteen thousand, five hundred cubic meters per hour per square meter surface (16,500 m³ph/m²). Moreover, the bodyside liner may be treated with a surfactant to provide a desired degree of wettability and hydrophilicity. The acquisition layer may be configured such that an air permeability of the acquisition layer is no less than twelve thousand cubic meters per hour per square meter surface (12,000 m³ph/m²). The absorbent core may also include superabsorbent material at no less than fifty percent (50%) by weight of a matrix of cellulosic fluff and superabsorbent material. Such properties of the bodyside liner, the acquisition layer, and the absorbent core may advantageously facilitate dryness, e.g., such that a second rewet of the absorbent article is less than three-tenths of a gram (0.3 g) according to a Rewet Test. Thus, the absorbent article may be more comfortable to wear relative to conventional absorbent articles, which do not provide the same degree of dryness.

It is to be understood by one of ordinary skill in the art that the present discussion is a description of exemplary embodiments only, and is not intended as limiting the broader aspects of the present disclosure.

When introducing elements of the present disclosure or the preferred embodiment(s) thereof, the articles "a", "an", "the" and "said" are intended to mean that there are one or more of the elements. As used herein, the terms "includes" and "including" are intended to be inclusive in a manner similar to the term "comprising." Similarly, the term "or" is generally intended to be inclusive (i.e., "A or B" is intended to mean "A or B or both"). Approximating language, as used herein throughout the specification and claims, is applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. For example, the approximating language may refer to being within a ten percent (10%) margin.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "add-on" refers herein to an amount of treatment on a substrate after drying. For instance, the add-on level percentage of a surfactant applied as a treatment to a substrate may be calculated with the following.

$$\text{Add-on level } (\%) = [\text{wet pick-up of solution}] \times$$
$$[\text{weight \% surfactant in solution}] =$$
$$\left[ \frac{\text{wet fabric weight minus dry fabric weight}}{\text{dry fabric weight}} \right] \times$$
$$[\text{weight \% surfactant in solution}]$$

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple fibers typically having fiber lengths less than about one hundred millimeters (100 mm). Bales of staple fibers can undergo an opening process to separate the fibers that are then sent to a carding process that separates and combs the fibers to align them in the machine direction after which the fibers are deposited onto a moving wire for further processing. Such webs are usually subjected to some type of bonding process, such as thermal bonding using heat and/or pressure. In addition to or in lieu thereof, the fibers can be subject to adhesive processes to bind the fibers together, such as by the use of powder adhesives. The carded web can be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "elastic" and derivatives thereof refers to materials or components that are generally capable of recovering their shape after deformation when the deforming force is removed. Specifically, as used herein, the term elastic or elastomeric is meant to be that property of any material or component which, upon application of a biasing force, permits that material or component to be stretchable to a stretched, biased length, which is at least about 125 percent, that is 1.25 times, its relaxed, unbiased length, and that will cause the material to recover at least 40 percent of its elongation upon release of the stretching, elongating force.

The term "fiber" generally refers to an elongated extrudate formed by passing a polymer through a forming orifice, such as a die. Unless noted otherwise, the term "fiber" includes both discontinuous fibers having a definite length and substantially continuous filaments. Substantially continuous filaments may, for instance, have a length much greater than their diameter, such as a length to diameter ratio ("aspect ratio") greater than about 15,000 to 1, and in some cases, greater than about 50,000 to 1. The fiber is "hollow" to such an extent that the fiber contains a hollow cavity extending along at least a portion of the fiber in the longitudinal direction. In some cases, the cavity may extend along the entire length of the fiber. Fiber diameters are usually expressed in microns or denier per fiber (dpf). Another frequently used expression of fiber diameter is denier, which is defined as grams per 9000 meters of a fiber. For example, the diameter of a polypropylene fiber given in microns may be converted to denier by squaring, and multiplying the result by 0.00629, thus, a fifteen-micron polypropylene fiber has a denier of about 1.42 ($15.\mathrm{sup}.2 \times 0.00629 = 1.415$).

The term "film" refers herein to a thermoplastic film made using an extrusion and/or forming process, such as a cast film or blown film extrusion process. The term includes apertured films, slit films, and other porous films that constitute liquid transfer films, as well as films that do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable. The term "meltblown" refers herein to fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers that can be continuous or discontinuous, are generally smaller than about 0.6 denier, and can be tacky and self-bonding when deposited onto a collecting surface.

The term "nonwoven" refers herein to materials and webs of material that are formed without the aid of a textile weaving or knitting process. The materials and webs of materials can have a structure of individual fibers, filaments, or threads (collectively referred to as "fibers") that can be interlaid, but not in an identifiable manner as in a knitted fabric. Nonwoven materials or webs can be formed from many processes, such as, but not limited to, meltblowing processes, spunbonding processes, carded web processes, etc. The basis weight of nonwoven webs is usually expressed in ounces of material per square yard (osy) or grams per square meter (gsm).

The term "pliable" refers herein to materials that are compliant and that will readily conform to the general shape and contours of a body of the wearer.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about fifteen (15) times its weight and, in an aspect, at least about thirty (30) times its weight, in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds, such as cross-linked polymers. Various conventional techniques may be employed to determine the quantitative amount of superabsorbent material within a test sample. Suitable analytical techniques include, for example, a sulfated ash measurement method, such as described in Vogel's Textbook of Quantitative Inorganic Analysis, Fourth edition, Longman Inc., 1978, pp. 479-481. Another suitable technique is an ion exchange method (e.g. sodium ion exchange), such as described in Treatise on Analytical Chemistry, Volume 1, Interscience Publishers, Inc., 1961, pp. 345-350. Further suitable techniques include atomic absorption methods, such as described in Vogel's Textbook of Quantitative Inorganic Analysis, Fourth edition, Longman Inc., 1978, pp. 810-845. The Encyclopedia of Industrial Chemical Analysis, Volume 18, Interscience Publishers, Inc., division of John Wiley & Sons, 1973, at pp. 207-259 further describes well known, conventional techniques for quantitatively measuring the amount of sodium within a sample. Another technique for determining the quantitative amount of superabsorbent material within test samples is an "on/off" method, which include forming a first set of samples (e.g., absorbent articles or absorbent cores) with superabsorbent material added to each of the first set of samples and forming a second set of samples (e.g., absorbent articles or absorbent cores) with superabsorbent material not added to each of the second set of samples. The first and second set of samples are both formed on the same line and/or with the same manufacturing process except that the flow of superabsorbent material on the line is "on" or active for the first set of samples and is "off" or inactive for the second set of samples. The mass or weight differential between the first and second sets of samples may be measured to determine the (e.g., average)

quantitative amount of superabsorbent material within the samples of the first set of samples.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Figure 2:
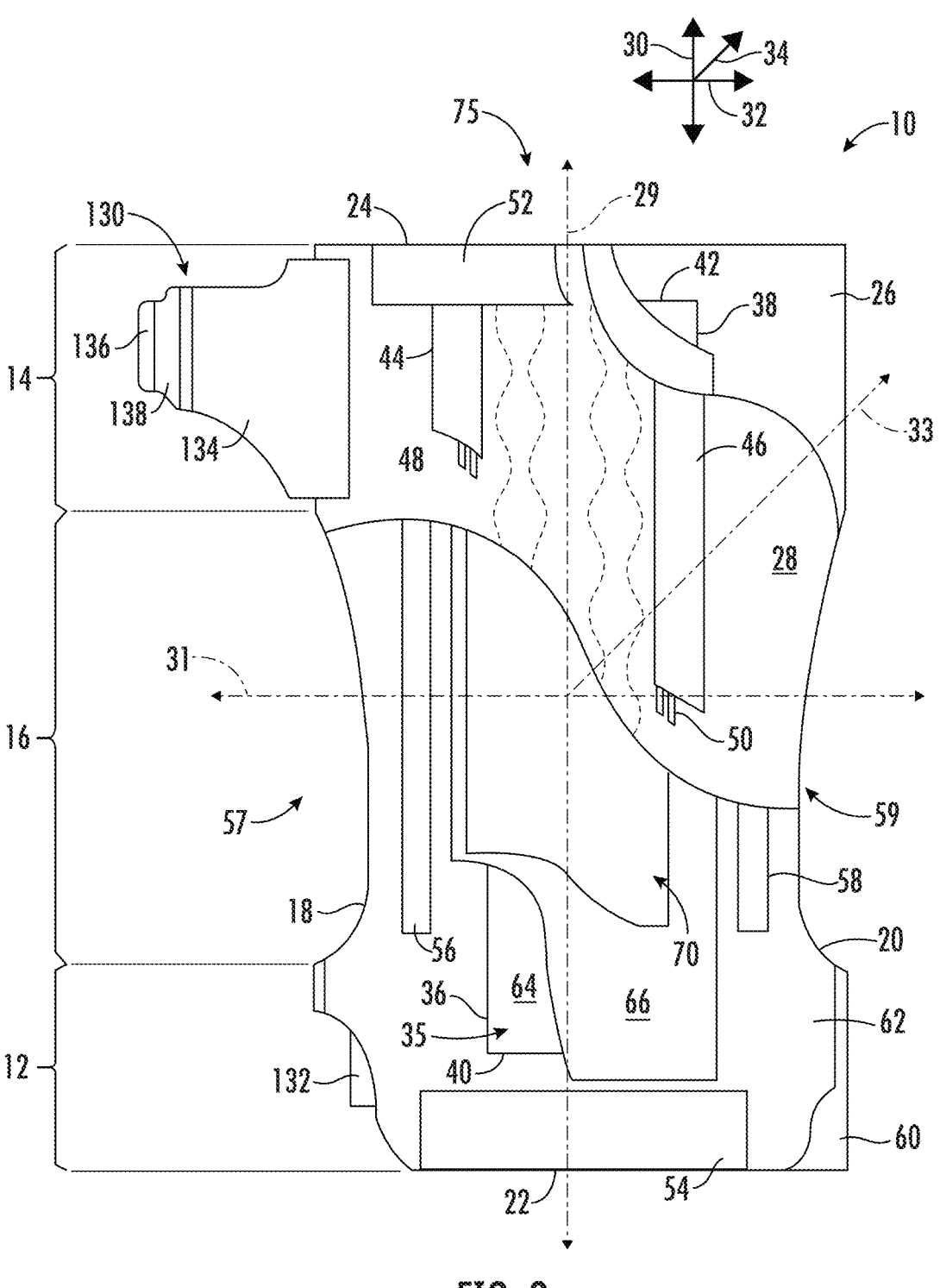
FIG. 2 is a top plan view of the example absorbent article of FIG. 1 in a stretched and laid flat arrangement, with portions of the example absorbent article being cut away for clarity of illustration.

Absorbent Article:

Referring to FIGS. 1 and 2, a non-limiting example of an absorbent article 10, in this case a diaper, is illustrated. Other absorbent articles include training pants, youth pants, adult incontinence garments, and feminine hygiene articles. While the example aspects and illustrations described herein can generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross-direction manufacturing of a product. The absorbent article 10 illustrated in FIGS. 1 and 2 includes a front waist region 12, a rear waist region 14, and a crotch region 16 disposed between the front waist region 12 and the rear waist region 14 and interconnecting the front and rear waist regions, 12, 14, respectively. The front waist region 12 may be referred to as the front-end region, the rear waist region 14 may be referred to as the rear-end region, and the crotch region 16 may be referred to as the intermediate region. The absorbent article 10 has a pair of longitudinal side edges, 18, 20, and a pair of opposite waist edges, respectively designated front waist edge 22 and rear waist edge 24. The front waist region 12 may be contiguous with the front waist edge 22, and the rear waist region 14 may be contiguous with the rear waist edge 24. The longitudinal side edges 18, 20 may extend from the front waist edge 22 to the rear waist edge 24.

The front waist region 12 may include the portion of the absorbent article 10 that, when worn, is positioned at least in part on the front of the wearer while the rear waist region 14 may include the portion of the absorbent article 10 that, when worn, is positioned at least in part on the back of the wearer. The crotch region 16 of the absorbent article 10 may include the portion of the absorbent article 10, that, when worn, is positioned between the legs of the wearer and may partially cover the lower torso of the wearer. The waist edges, 22 and 24, of the absorbent article 10 are configured to encircle the waist of the wearer and together define the central waist opening 23. Portions of the longitudinal side edges, 18 and 20, in the crotch region 16 may generally define leg openings when the absorbent article 10 is worn.

The absorbent article 10 may include a backsheet 26 and a bodyside liner 28. In an example aspect, the bodyside liner 28 may be bonded to the backsheet 26 in a superposed relation by any suitable mechanism such as, but not limited to, adhesives, ultrasonic bonds, thermal bonds, pressure bonds, or other conventional techniques. The backsheet 26 may define a length in a longitudinal direction 30 and a width in the lateral direction 32, which, in the illustrated aspect, may coincide with the length and width of the absorbent article 10. As illustrated in FIG. 2, the absorbent article 10 may have a longitudinal axis 29 extending in the longitudinal direction 30 and a lateral axis 31 extending in the lateral direction 32. The longitudinal axis 29 and the lateral axis 31 may define a plane. The absorbent article 10 may also have a transverse axis 33 extending in a transverse direction 34. The transverse axis 33 is perpendicular to the plane defined by the longitudinal axis 29 and the lateral axis 31.

FIG. 2 illustrates the absorbent article 10 with certain portions cut-away for illustrating additional aspects of the absorbent article 10. An absorbent body 35 may be disposed between the backsheet 26 and the bodyside liner 28. The absorbent body 35 may have longitudinal edges, 36 and 38, which, in an example aspect, may form portions of the longitudinal side edges, 18 and 20, respectively, of the absorbent article 10 and may have opposite end edges, 40 and 42, which, in an example aspect, may form portions of the waist edges, 22 and 24, respectively, of the absorbent article 10. In an example aspect, the absorbent body 35 may have a length and width that are the same as or less than the length and width of the absorbent article 10. The absorbent article 10 may also include a fluid acquisition layer 70 and a fluid transfer layer 66.

The absorbent article 10 may be configured to contain and/or absorb liquid, solid, and semi-solid body exudates discharged from the wearer. For example, containment flaps, 44 and 46, may be configured to provide a barrier to the lateral flow of body exudates. As illustrated in FIG. 2, each containment flap 44, 46 may include elastic members 48, 50. The elastic members 48, 50 may include one or more elastic strands (two are shown in FIG. 2) that are aligned substantially parallel to the longitudinal axis 29 of the absorbent article 10. The containment flaps 44, 46 are laterally spaced from each other, such that the containment flap 44 is on one side of the longitudinal axis 29 and the containment flap 46 is on an opposite side of the longitudinal axis 29. The containment flaps 44, 46 may be attached to the absorbent article 10 by being bonded to the bodyside liner 28. The containment flaps, 44 and 46, may be located laterally inward from the longitudinal side edges, 18, 20 of the absorbent article 10 and may extend longitudinally along the entire length of absorbent article 10 or may extend partially along the length of the absorbent article 10.

To further enhance containment and/or absorption of body exudates, in some example aspects, the absorbent article 10 may suitably include a rear waist elastic member 52, a front waist elastic member 54, and leg elastic members, 56 and 58, as are known to those skilled in the art. The waist elastic members, 52 and 54, may be attached to the backsheet 26 and/or the bodyside liner 28 along the opposite waist edges, 24 and 22, and may extend over part or all of the waist edges, 24 and 22. In an example aspect shown in FIG. 2, the rear waist elastic member 52 is attached to the bodyside liner 28 and the containment flaps 44, 46 and the front waist elastic member 54 is attached to the backsheet 26. The leg elastic members, 56 and 58, may be attached to the backsheet 26 and/or the bodyside liner 28 along the opposite longitudinal side edges, 18 and 20, and positioned in the crotch region 16 of the absorbent article 10.

The backsheet 26 and/or portions thereof may be breathable and/or liquid impermeable. The backsheet 26 and/or portions thereof may be elastic, stretchable, or non-stretchable. The backsheet 26 may be constructed of a single layer, multiple layers, laminates, spunbond fabrics, films, meltblown fabrics, elastic netting, microporous webs, bonded-carded webs or foams provided by elastomeric or polymeric materials. In an example aspect, for example, the backsheet 26 may be constructed of a microporous polymeric film, such as polyethylene or polypropylene.

In an example aspect, the backsheet 26 may be a single layer of a liquid impermeable material. In an example aspect, the backsheet 26 may be suitably stretchable, and more suitably elastic, in at least the lateral or circumferential direction 32 of the absorbent article 10. In an example aspect, the backsheet 26 may be stretchable, and more suitably elastic, in both the lateral 32 and the longitudinal 30 directions. In an example aspect, the backsheet 26 may be a multi-layered laminate, in which at least one of the layers is liquid impermeable. In an example aspect, the backsheet 26 may be a two layer construction, including an outer layer material 60 and an inner layer material 62 that may be bonded together, such as by a laminate adhesive. Suitable laminate adhesives may be applied continuously or intermittently as beads, a spray, parallel swirls, or the like, but it is to be understood that the inner layer 62 may be bonded to the outer layer 60 by other bonding methods, including, but not limited to, ultrasonic bonds, thermal bonds, pressure bonds, or the like.

The outer layer 60 of the backsheet 26 may be any suitable material and may be one that provides a generally cloth-like texture or appearance to the wearer. An example of such material may be a one hundred percent (100%) polypropylene bonded-carded web with a diamond bond pattern available from Sandler A. G., Germany, such as thirty (30) gsm Sawabond 4185® or equivalent. Another example of material suitable for use as an outer layer 60 of a backsheet 26 may be a twenty (20) gsm spunbond polypropylene non-woven web.

The liquid impermeable inner layer 62 of the backsheet 26 (or the liquid impermeable backsheet 26 where the backsheet 26 is of a single-layer construction) may be either vapor permeable (i.e., "breathable") or vapor impermeable. The liquid impermeable inner layer 62 (or the liquid impermeable backsheet 26 where the backsheet 26 is of a single-layer construction) may be manufactured from a thin plastic film, although other liquid impermeable materials may also be used. The liquid impermeable inner layer 62 (or the liquid impermeable backsheet 26 where the backsheet 26 is of a single-layer construction) can inhibit liquid body exudates from leaking out of the absorbent article 10 and wetting articles, such as bed sheets and clothing, as well as the wearer and caregiver. An example of a material for a liquid impermeable inner layer 62 (or the liquid impermeable backsheet 26 where the backsheet 26 is of a single-layer construction) may be a printed nineteen (19) gsm Berry Plastics XP-8695H film or equivalent commercially available from Berry Plastics Corporation, Evansville, IN, U.S.A.

Where the backsheet 26 is of a single layer construction, the backsheet 26 may be embossed and/or matte finished to provide a more cloth-like texture or appearance. The backsheet 26 may permit vapors to escape from the absorbent article 10 while preventing liquids from passing through. A suitable liquid impermeable, vapor permeable material may be composed of a microporous polymer film or a non-woven material that has been coated or otherwise treated to impart a desired level of liquid impermeability.

The absorbent body 35 may be suitably constructed to be generally compressible, conformable, pliable, non-irritating to the skin of the wearer and capable of absorbing and retaining liquid body exudates. The absorbent body 35 may be manufactured in a wide variety of sizes and shapes (for example, rectangular, trapezoidal, T-shape, I-shape, hourglass shape, etc.) and from a wide variety of materials. The size and the absorbent capacity of the absorbent body 35 should be compatible with the size of the intended wearer (infants to adults) and the liquid loading imparted by the intended use of the absorbent article 10. The absorbent body 35 may have a length and width that may be less than or equal to the length and width of the absorbent article 10. The absorbent body 35 may have two surfaces such as a wearer facing surface 64 and a garment facing surface (not shown). Edges, such as longitudinal side edges, 36 and 38 and such as front and back end edges, 40 and 42, may connect the two surfaces.

In an example aspect, the absorbent body 35 may include a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an example aspect, the absorbent body 35 may be a matrix of cellulosic fluff and superabsorbent material. In an example aspect, the absorbent body 35 may be constructed of a single layer of materials, or in the alternative, may be constructed of two or more layers of materials.

Various types of wettable, hydrophilic fibers may be used in the absorbent body 35. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers that have been hydrophilized by suitable mechanisms. The fibers may be hydrophilized, for example, by treatment with a surfactant, treatment with silica, treatment with a material that has a suitable hydrophilic moiety and is not readily removed from the fiber, or by sheathing the nonwettable, hydrophobic fiber with a hydrophilic polymer during or after formation of the fiber. Suitable superabsorbent materials may be selected from natural, synthetic, and modified natural polymers and materials. The superabsorbent materials may be inorganic materials, such as silica gels, or organic compounds, such as cross-linked polymers.

The absorbent body 35 may be superposed over the inner layer 62 of the backsheet 26, extending laterally between the leg elastic members, 56, 58, and may be bonded to the inner layer 62 of the backsheet 26, such as by being bonded thereto with adhesive. However, it is to be understood that the absorbent body 35 may be in contact with, and not bonded with, the backsheet 26 and remain within the scope of this disclosure. In an example aspect, the backsheet 26 may be composed of a single layer and the absorbent body 35 may be in contact with the single layer of the backsheet 26. In an example aspect, a layer, such as but not limited to, a fluid transfer layer 66, may be positioned between the absorbent body 35 and the backsheet 26.

In various example aspects, an absorbent article 10 may be constructed without a fluid transfer layer 66. In various example aspects, the absorbent article 10 may have a fluid transfer layer 66. In an example aspect, the fluid transfer layer 66 may be in contact with the absorbent body 35. In an example aspect, the fluid transfer layer 66 may be bonded to the absorbent body 35. Bonding of the fluid transfer layer 66 to the absorbent body 35 may occur via any mechanism known to one of ordinary skill, such as, but not limited to, adhesives. In an example aspect, a fluid transfer layer 66 may be positioned between the bodyside liner 28 and the absorbent body 35. In an example aspect, a fluid transfer layer 66 may completely encompass the absorbent body 35 and may be sealed to itself. In an example aspect, a fluid transfer layer 66 may be composed of separate sheets of material that may be utilized to partially or fully encompass the absorbent body 35 and that may be sealed together using sealing mechanisms, such as, but not limited to, an ultrasonic bonder or other thermochemical bonder or the use of an adhesive. In an example aspect, the fluid transfer layer 66 may be in contact with and/or bonded with the wearer facing surface 64 of the absorbent body 35.

The fluid transfer layer 66 may be pliable, less hydrophilic than the absorbent body 35, and sufficiently porous to thereby permit liquid body exudates to penetrate through the fluid transfer layer 66 to reach the absorbent body 35. In an example aspect, the fluid transfer layer 66 may have sufficient structural integrity to withstand wetting thereof and of the absorbent body 35. In an example aspect, the fluid transfer layer 66 may be constructed from a single layer of material or the fluid transfer layer 66 may be a laminate constructed from two or more layers of material. In an example aspect, the fluid transfer layer 66 may include, but is not limited to, natural and synthetic fibers, such as, but not limited to, polyester, polypropylene, acetate, nylon, polymeric materials, cellulosic materials and combinations thereof. In an example aspect, a fluid transfer layer 66 may include spunbond and/or meltblown materials. In an example aspect, the fluid transfer layer 66 may be a laminate of a meltblown nonwoven material having fine fibers laminated to at least one spunbond nonwoven material layer having coarse fibers. In such an example aspect, the fluid transfer layer 66 may be a spunbond-meltblown ("SM") material, while in other example aspects, the fluid transfer layer 66 may be a spunbond-meltblown-spunbond ("SMS") material. In various example aspects, the fluid transfer layer 66 may be hydrophilic. In various example aspects, the fluid transfer layer 66 may be hydrophobic and may be treated in any manner known in the art to be made hydrophilic. In an example aspect, the fluid transfer layer 66 may have a longitudinal length the same as, greater than, or less than the longitudinal length of the absorbent body 35.

In various example aspects, the absorbent article 10 may have a fluid acquisition layer 70. The acquisition layer 70 can help decelerate and diffuse surges or gushes of liquid body exudates penetrating the bodyside liner 28. In an example aspect, the acquisition layer 70 may be positioned between the bodyside liner 28 and the backsheet 26. In an example aspect, the acquisition layer 70 may be positioned between the bodyside liner 28 and the absorbent body 35 to take in and distribute body exudates for absorption by the absorbent body 35. In an example aspect, the acquisition layer 70 may be positioned between the bodyside liner 28 and a fluid transfer layer 66 if a fluid transfer layer 66 is present.

In an example aspect, the acquisition layer 70 may be in contact with and/or bonded with the bodyside liner 28. In an example aspect in which the acquisition layer 70 is bonded with the bodyside liner 28, bonding of the acquisition layer 70 to the bodyside liner 28 may occur through the use of an adhesive and/or point fusion bonding, but is not limited to such methods of bonding. For example, the bodyside liner 28 may be bonded to the acquisition layer 70 by hydroentangling the bodyside liner 28 with the acquisition layer 70. The point fusion bonding may be selected from, but is not limited to, ultrasonic bonding, pressure bonding, thermal bonding, and combinations thereof. In an example aspect, the point fusion bonding may be provided in any pattern as deemed suitable. As an example, the bodyside liner 28 may be bonded to the acquisition layer 70 at a range of one percent to ninety percent (1%-90%). The percentage of bonding between the bodyside liner 28 and the acquisition layer 70 may be measured by calculating the area of bonded material between the bodyside liner 28 and the acquisition layer 70 and dividing by the area of overlap between the bodyside liner 28 and the acquisition layer 70 as viewed from the transverse direction 34 perpendicular to both the longitudinal and lateral directions 30, 32, as in a dimension that is perpendicular to the plane of the bodyside liner 28 when the bodyside liner 28 is laid flat.

The acquisition layer 70 may be rectangular in shape, or may be any other shape. The acquisition layer 70 may have any longitudinal length dimension as deemed suitable. For example, the acquisition layer 70 may have a longitudinal length shorter than, the same as, or longer than the longitudinal length of the absorbent body 35. In an example aspect, the acquisition layer 70 may have any length such that the acquisition layer 70 may be coterminous with the waist edges, 22 and 24, of the absorbent article 10. In an example aspect, the longitudinal length of the acquisition layer 70 may be the same as the longitudinal length of the absorbent body 35. In such an example aspect, the midpoint of the longitudinal length of the acquisition layer 70 may substantially align with the midpoint of the longitudinal length of the absorbent body 35.

In an example aspect, the longitudinal length of the acquisition layer 70 may be shorter than the longitudinal length of the absorbent body 35. In such an example aspect, the acquisition layer 70 may be positioned at any desired location along the longitudinal length of the absorbent body 35. As an example of such an aspect, the absorbent article 10 may contain a target zone where repeated liquid surges typically occur in the absorbent article 10. The particular location of a target zone may vary depending on the age and gender of the wearer of the absorbent article 10. For example, males tend to urinate further toward the front waist region 12 of the absorbent article 10 and the target zone may be phased forward within the absorbent article 10. For example, the target zone for a male wearer may be positioned about seven centimeters (7 cm) forward of the longitudinal midpoint of the absorbent body 35 and may have a length of about plus or minus seven and a half centimeters (±7.5 cm) and a width of about plus or minus five centimeters (±5 cm). The female target zone may be located closer to the center of the crotch region 16 of the absorbent article 10. For example, the target zone for a female wearer may be positioned about two and a half centimeters (2.5 cm) forward of the longitudinal midpoint of the absorbent body 35 and may have a length of about plus or minus seven and a half centimeters (±7.5 cm) and a width of about plus or minus five centimeters (±5 cm). As a result, the relative longitudinal placement of the acquisition layer 70 within the absorbent article 10 may be selected to best correspond with the target zone of either or both categories of wearers.

In an example aspect, the absorbent article 10 may contain a target zone centered within the crotch region 16 of the absorbent article 10. The acquisition layer 70, therefore, may be positioned along the longitudinal length of the absorbent article 10 such that the acquisition layer 70 may be substantially aligned with the target zone of the absorbent article 10. Alternatively, the absorbent article 10 may contain a target zone positioned between the crotch region 16 and the front waist region 12 of the absorbent article 10. The acquisition layer 70, therefore, may be positioned along the longitudinal length of the absorbent article 10 such that the acquisition layer 70 can be substantially aligned with the target zone of the absorbent article 10. In an example aspect, the acquisition layer 70 may have a size dimension that is the same size dimension as the target zone of the absorbent article 10 or a size dimension greater than the size dimension of the target zone of the absorbent article 10. In an example aspect, the acquisition layer 70 may be in contact with and/or bonded with the bodyside liner 28 at least partially in the target zone of the absorbent article 10.

In various example aspects, the acquisition layer 70 may have a longitudinal length shorter than, the same as, or longer than, the longitudinal length of the absorbent body 35. In an example aspect in which the absorbent article 10 is a diaper, the acquisition layer 70 may have a longitudinal length from about one hundred and twenty millimeters (120 mm), about one hundred and thirty millimeters (130 mm), about one hundred and forty millimeters (140 mm), about one hundred and fifty millimeters (150 mm), about one hundred and sixty millimeters (160 mm), about one hundred and seventy millimeters (170 mm), or about one hundred and eighty millimeters (180 mm) to about two hundred millimeters (200 mm), about two hundred and ten millimeters (210 mm), about two hundred and twenty millimeters (220 mm), about two hundred and thirty millimeters (230 mm), about two hundred and forty millimeters (240 mm), about two hundred and sixty millimeters (260 mm), about two hundred and eighty millimeters (280), about three hundred millimeters (300 mm), about three hundred and ten millimeters (310 mm), or about three hundred and twenty millimeters (320 mm). In such an example aspect, the acquisition layer 70 may be shorter in longitudinal length than the longitudinal length of the absorbent body 35 and may be phased from the front end edge 40 of the absorbent body 35 by a distance of from about fifteen millimeters (15 mm), about twenty millimeters (20 mm), or about twenty-five millimeters (25 mm) to about thirty millimeters (30 mm), about thirty-five millimeters (35 mm), or about forty millimeters (40 mm). In an example aspect in which the absorbent article 10 may be a training pant or youth pant, the acquisition layer 70 may have a longitudinal length from about one hundred and twenty millimeters (120 mm), about one hundred and thirty millimeters (130 mm), about one hundred and forty millimeters (140 mm), about one hundred and fifty millimeters (150 mm), about two hundred (200 mm), about two hundred and ten millimeters (210 mm), about two hundred and twenty millimeters (220 mm), about two hundred and thirty millimeters (230 mm), about two hundred and forty millimeters (240 mm), or about two hundred and fifty millimeters (250 mm) to about two hundred and sixty millimeters (260 mm), about two hundred and seventy millimeters (270 mm), about two hundred and eighty millimeters (280 mm), about two hundred and ninety millimeters (290 mm), about three hundred millimeters (300 mm), about three hundred and forty millimeters (340 mm), about three hundred and sixty millimeters (360 mm), about four hundred millimeters (400 mm), about four hundred and ten millimeters (410 mm), about four hundred and twenty millimeters (420 mm), about four hundred and thirty millimeters (430 mm), about four hundred and forty millimeters (440 mm), about four hundred and fifty millimeters (450 mm), about four hundred and sixty millimeters (410 mm), about four hundred and eighty millimeters (480 mm), about five hundred millimeters (500 mm), about five hundred and ten millimeters (510 mm), or about five hundred and twenty millimeters (520 mm). In such an example aspect, the acquisition layer 70 may have a longitudinal length shorter than the longitudinal length of the absorbent body 35 and may be spaced a distance of from about twenty-five millimeters (25 mm), about thirty millimeters (30 mm), about thirty-five millimeters (35 mm), or about forty millimeters (40 mm) to about forty-five millimeters (45 mm), about fifty millimeters (50 mm), about fifty-five millimeters (55 mm), about sixty millimeters (60 mm), about sixty-five millimeters (65 mm), about seventy millimeters (70 mm), about seventy-five millimeters (75 mm), about eighty millimeters (80 mm), or about eighty-five millimeters (85 mm) from the front end edge 40 of the absorbent body 35. In an example aspect in which the absorbent article 10 is an adult incontinence garment, the acquisition layer 70 may have a longitudinal length from about two hundred (200 mm), about two hundred and ten millimeters (210 mm), about two hundred and twenty millimeters (220 mm), about two hundred and thirty millimeters (230 mm), about two hundred and forty millimeters (240 mm), or about two hundred and fifty millimeters (250 mm) to about two hundred and sixty millimeters (260 mm), about two hundred and seventy millimeters (270 mm), about two hundred and eighty millimeters (280 mm), about two hundred and ninety millimeters (290 mm), about three hundred millimeters (300 mm), about three hundred and forty millimeters (340 mm), about three hundred and sixty millimeters (360 mm), about four hundred millimeters (400 mm), about four hundred and ten millimeters (410 mm), about four hundred and fifteen millimeters (415 mm), about four hundred and twenty-five millimeters (425 mm), or about four hundred and fifty millimeters (450 mm). In such an example aspect, the acquisition layer 70 may have a longitudinal length shorter than the longitudinal length of the absorbent body 35 and the acquisition layer 70 may be phased a distance of from about twenty millimeters (20 mm), about twenty-five millimeters (25 mm), about thirty millimeters (30 mm), or about thirty-five millimeters (35 mm) to about forty millimeters (40 mm), about forty-five millimeters (45 mm), about fifty millimeters (50 mm), about fifty-five millimeters (55 mm), about sixty millimeters (60 mm), about sixty-five millimeters (65 mm), about seventy millimeters (70 mm), or about seventy-five millimeters (75 mm) from the front end edge 40 of the absorbent body 35.

The acquisition layer 70 may have any width as desired. The width of the acquisition layer 70 may vary dependent upon the size and shape of the absorbent article 10 within which the acquisition layer 70 will be placed. The acquisition layer 70 may have a width smaller than, the same as, or larger than the width of the absorbent body 35. Within the crotch region 16 of the absorbent article 10, the acquisition layer 70 may have a width smaller than, the same as, or larger than the width of the absorbent body 35.

The acquisition layer 70 may have a body facing surface and a garment facing surface. The acquisition layer 70 may have at least one aperture or a plurality of apertures (not shown). In some example aspects, the apertures may extend from the body facing surface of the acquisition layer 70 to the garment facing surface of the acquisition layer 70. The plurality of apertures may be in a pattern.

The bodyside liner 28 of the absorbent article 10 may overlay the absorbent body 35 and the backsheet 26 and can isolate the skin of the wearer from liquid waste retained by the absorbent body 35. In various example aspects, a fluid transfer layer 66 may be positioned between the bodyside liner 28 and the absorbent body 35. In various example aspects, an acquisition layer 70 may be positioned between the bodyside liner 28 and the absorbent body 35 or a fluid transfer layer 66, if present. In various example aspects, the bodyside liner 28 may be bonded to the acquisition layer 70, or to the fluid transfer layer 66 if no acquisition layer 70 is present, via adhesive and/or by a point fusion bonding. The point fusion bonding may be selected from ultrasonic, thermal, pressure bonding, and combinations thereof.

In an example aspect, the bodyside liner 28 may extend beyond the absorbent body 35 and/or a fluid transfer layer 66, and/or an acquisition layer 70 to overlay a portion of the backsheet 26 and may be bonded thereto by any method deemed suitable, such as, for example, by being bonded thereto by adhesive, to substantially enclose the absorbent body 35 between the backsheet 26 and the bodyside liner 28. The bodyside liner 28 may be narrower than the backsheet 26, but it is to be understood that the bodyside liner 28 and the backsheet 26 may be of the same dimensions. It is also contemplated that the bodyside liner 28 may not extend beyond the absorbent body 35 and/or may not be secured to the backsheet 26. It is further contemplated that the bodyside liner 28 may be composed of more than one segment of material. The bodyside liner 28 may be of different shapes, including rectangular, hourglass, or any other shape. The bodyside liner 28 may be suitably compliant, soft feeling, and non-irritating to the skin of the wearer skin and may be the same as or less hydrophilic than the absorbent body 35 to permit body exudates to readily penetrate through to the absorbent body 35 and provide a relatively dry surface to the wearer.

The bodyside liner 28 may be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics may be used for the bodyside liner 28. The bodyside liner 28 may include a woven fabric, a nonwoven fabric, a polymer film, a film-fabric laminate or the like, as well as combinations thereof. Examples of a nonwoven fabric may include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, may include more than one layer of fabrics, films, and/or webs, as well as combinations thereof. For example, the bodyside liner 28 may include a support layer and a projection layer that may be hydroentangled.

For example, the bodyside liner 28 may include melt-blown or spunbond web of polyolefin fibers. Alternatively, the bodyside liner 28 may be a bonded-carded web composed of natural and/or synthetic fibers. The bodyside liner 28 may be composed of a substantially hydrophobic material, and the hydrophobic material may, optionally, be treated with a surfactant or otherwise processed to impart a desired level of wettability and hydrophilicity. The surfactant may be applied by any conventional mechanism, such as spraying, printing, brush coating, foaming, kiss roll, or the like. The surfactant may be applied to the entire bodyside liner 28 or the surfactant may be selectively applied to particular sections of the bodyside liner 28.

In an example aspect, a bodyside liner 28 may be constructed of a non-woven bicomponent web. The non-woven bicomponent web may be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, and end-to-end may be used without departing from the scope of this disclosure. In an example aspect, a bodyside liner 28 may be a spunbond substrate with a basis weight from about ten (10) or twelve (12) gsm to about fifteen (15) or twenty (20) gsm. In an example aspect, a bodyside liner 28 may be a twelve (12) gsm spunbond-meltblown-spunbond substrate having ten percent (10%) meltblown content applied between the two spunbond layers.

Although the backsheet 26 and bodyside liner 28 may include elastomeric materials, it is contemplated that the backsheet 26 and the bodyside liner 28 include materials that are generally non-elastomeric. In an example aspect, the bodyside liner 28 may be stretchable, and more suitably elastic. In an example aspect, the bodyside liner 28 may be suitably stretchable and more suitably elastic in at least the lateral or circumferential direction of the absorbent article 10. In other example aspects, the bodyside liner 28 may be stretchable, and more suitably elastic, in both the lateral and the longitudinal directions 32, 30, respectively.

In an example aspect, containment flaps, 44, 46, may be secured to the bodyside liner 28 of the absorbent article 10 in a generally parallel, spaced relation with each other laterally inward of the leg openings to provide a barrier against the flow of body exudates. In an example aspect, the containment flaps, 44, 46, may extend longitudinally from the front waist region 12 of the absorbent article 10, through the crotch region 16 to the back waist region 14 of the absorbent article 10. The containment flaps 44, 46 may be bonded to the bodyside liner 28 with adhesive or other mechanisms as are known in the art. Alternatively, each containment flap 44, 46 may be bonded to other components of the absorbent article 10 other than the bodyside liner 28, including, but not limited to, the backsheet 26.

The containment flaps, 44 and 46, may be constructed of a fibrous material that may be similar to the material forming the bodyside liner 28. Other conventional materials, such as polymer films, may also be employed. Each containment flap, 44 and 46, may include flap elastics, such as flap elastics 48 and 50, respectively. Suitable elastic materials for the flap elastic, 48 and 50, may include sheets, strands or ribbons of natural rubber, synthetic rubber, or thermoplastic elastomeric materials. The flap elastics, 48 and 50, as illustrated, may have two strands of elastomeric material extending longitudinally along the containment flaps, 44 and 46, in generally parallel, spaced relation with each other. The elastic strands may be within the containment flaps, 44 and 46, while in an elastically contractible condition such that contraction of the strands gathers and shortens the containment flaps, 44 and 46. As a result, the elastic strands can bias the containment flaps, 44 and 46, toward a position spaced from a position of where the containment flaps, 44 and 46, are bonded to absorbent article 10 such that a portion of the containment flaps, 44 and 46, extend away from the bodyside liner 28 in a generally upright orientation of the containment flaps, 44 and 46, especially in the crotch region 16 of the absorbent article 10, when the absorbent article 10 is fitted on the wearer. The containment flaps, 44 and 46, may be connected to the flap elastics, 48 and 50, by partially doubling a portion of the containment flap, 44 and 46, material back upon itself by an amount sufficient to enclose the flap elastics, 48 and 50. It is to be understood, however, that the containment flaps, 44 and 46, may have any number of strands of elastomeric material and may also be omitted from the absorbent article 10 without departing from the scope of this disclosure.

Leg elastic members 56, 58 may be secured to the backsheet 26, such as by being bonded thereto by laminate adhesive, generally laterally inward of the longitudinal side edges, 18 and 20, of the absorbent article 10. The leg elastic members 56, 58 may form elasticized leg cuffs 57, 59, respectively, that further help to contain body exudates. In an example aspect, the leg elastic members 56, 58 may be disposed between the inner layer 62 and outer layer 60 of the backsheet 26 or between other layers of the absorbent article 10. The leg elastic members 56, 58 may be a single elastic member as illustrated in the figures herein, or each leg elastic member 56, 58 may include more than one elastic member. A wide variety of elastic materials may be used for the leg elastic members 56, 58. Suitable elastic materials may include sheets, strands or ribbons of natural rubber, synthetic rubber, or thermoplastic elastomeric materials. The elastic materials may be stretched and secured to a substrate, secured to a gathered substrate, or secured to a substrate and then elasticized or shrunk, for example, with the application of heat, such that the elastic retractive forces are imparted to the substrate.

In an example aspect, the absorbent article 10 may include a fastener system. The fastener system may include one or more back fasteners 130 and one or more front fasteners 132. Portions of the fastener system may be included in the front waist region 12, back waist region 14, or both. The fastener system may be configured to secure the absorbent article 10 about the waist of the wearer and maintain the absorbent article 10 in place during use. In an example aspect, the back fasteners 130 may include one or more materials bonded together to form a composite ear as is known in the art. For example, the composite fastener may be composed of a stretch component 134, a nonwoven carrier or hook base 136, and a fastening component 138.

In an example aspect, the absorbent article 10 may have waist elastic members, 52 and 54, which may be formed of any suitable elastic material. The waist elastic member 52 may be in a rear waist region 14 of the absorbent article 10 and the waist elastic member 54 may be in a front waist region 12 of the absorbent article 10. Suitable elastic materials for the waist elastic members 52, 54 may include, but are not limited to, sheets, strands or ribbons of natural rubber, synthetic rubber, or thermoplastic elastomeric polymers. The elastic materials may be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 52 and 54, may be omitted from the absorbent article 10 without departing from the scope of this disclosure.

Fluid Control:

The bodyside liner 28, absorbent body 35, and acquisition layer 70 may have various advantageous properties to facilitate fluid flow within the target zone. For instance, the bodyside liner 28, absorbent body 35, and acquisition layer 70 may be configured for limiting or preventing liquid and semi-solid body exudates discharged from the wearer from moving outside of the target zone, which can advantageously provide desired dryness. Thus, the absorbent article 10 may be more comfortable to wear relative to conventional absorbent articles, which do not provide the same degree of dryness.

As an example, the bodyside liner 28 may have a relatively high permeability, which can be indicated by measuring air permeability. The air permeability of the bodyside liner 28, for instance, may be no less than thirteen thousand cubic meters per hour per square meter surface (13,000 $m^3ph/m^2$), such as no less than fourteen thousand, five hundred cubic meters per hour per square meter surface (14,500 $m^3ph/m^2$), and no greater than sixteen thousand, five hundred cubic meters per hour per square meter surface (16,500 $m^3ph/m^2$). The above-described air permeability of the bodyside liner 28 may advantageously provide improved dryness (e.g., via lower rewet) and reduced fluid intake time relative to bodyside liners with relatively low permeability and lesser air permeability.

Various characteristics of the bodyside liner 28, such as basis weight, fiber size, and bond pattern area, may be selected to provide the desired air permeability for the bodyside liner 28. For example, the basis weight of the bodyside liner 28 may be no less than ten grams per square meter (10 gsm) and no greater than twenty grams per square meter (20 gsm), such as no less than eleven grams per square meter (11 gsm) and no greater than sixteen grams per square meter (16 gsm), such as no less than twelve grams per square meter (12 gsm) and no greater than fifteen grams per square meter (15 gsm), such as about fourteen grams per square meter (14 gsm). As another example, the bodyside liner 28 may include a spunbond web of fibers, such as polypropylene fibers. Thus, e.g., the bodyside liner 28 may be a spunbond polypropylene non-woven web, e.g., with a basis weight no less than twelve grams per square meter (12 gsm) and no greater than fifteen grams per square meter (15 gsm). As another example, diameters of the fibers in the spunbond bodyside liner 28 may be no less than one and two-tenths denier per filament (1.2 dpf) and no greater than two denier per filament (2 dpf), such as about one and six-tenths denier per filament (1.6 dpf). It will be understood that the bodyside liner 28 may be formed from fibers with different compositions and/or using different nonwoven techniques in other example embodiments.

As an example, the bodyside liner 28 may be treated to adjust the wettability and hydrophilicity of the bodyside liner 28. For example, the bodyside liner 28 may be treated with a surfactant or otherwise processed to impart a desired level of wettability and hydrophilicity. The surfactant may be applied by any conventional mechanism, such as spraying, printing, brush coating, foaming, kiss roll, or the like. The surfactant may be applied to the entire bodyside liner 28 or the surfactant may be selectively applied to particular sections of the bodyside liner 28, such as at the target zone. In example embodiments, the bodyside liner 28 may be treated with the surfactant at a minimum level to avoid harming fluid intake or runoff. For instance, the surfactant may be applied to the bodyside liner 28 to provide an add-on no less than two-tenths percent (0.2%) and no greater than one percent (1%). Moreover, for a "semi-treated" application, the surfactant may be applied to the bodyside liner 28 to provide an add-on level no less than three-tenths percent (0.3%) and no greater than five-tenths percent (0.5%), such as no greater than four-tenths percent (0.4%). For a "fully-treated" application, the surfactant may be applied to the bodyside liner 28 to provide an add-on of about eight-tenths percent (0.8%). Very high surfactant levels are more easily washed away and provide little added wettability, while very low levels may not impart sufficient wettability to the bodyside liner 28. In some example embodiments, fluid may be less attracted to a semi-treated bodyside liner 28 as compared to a fully-treated bodyside liner 28. Thus, e.g., the fluid may spread less on the semi-treated bodyside liner 28 and move towards the underlying acquisition layer 70, which may be more wettable than the semi-treated bodyside liner 28. This can result in the semi-treated bodyside liner 28 providing a lower rewet value than the fully-treated bodyside liner 28 but with a slower intake time. In certain example embodiments, the surfactant may include one or more non-ionic surfactants, such as hydrogenated ethoxylated castor oil and sorbitan monooleate, and/or anionic surfactants, such as proprietary blends of synthetic surfactant solutions commercially available, for example, from Schill & Seilacher AG. As an example, the acquisition layer 70 may also have a relatively high void volume, which can be indicated by measuring air permeability. The air permeability of the acquisition layer 70, for instance, may be no less than eleven thousand, nine hundred cubic meters per hour per square meter surface (11,900 $m^3$ph/$m^2$) and no greater than eighteen thousand, three hundred cubic meters per hour per square meter surface (18,300 $m^3$ph/$m^2$), such as no less than twelve thousand, seven hundred cubic meters per hour per square meter surface (12,700 $m^3$ph/$m^2$) and no greater than fourteen thousand, five hundred cubic meters per hour per square meter surface (14,500 $m^3$ph/$m^2$). In other units, the air permeability of the acquisition layer 70, for instance, may be no less than six hundred and fifty cubic feet per minute per square foot (650 $ft^3$pmin/$ft^2$) and no greater than one thousand cubic feet per minute per square foot (1000 $ft^3$pmin/$ft^2$), such as no less than seven hundred cubic feet per minute per square foot (700 $ft^3$pmin/$ft^2$) and no greater than nine hundred cubic feet per minute per square foot (900 $ft^3$pmin/$ft^2$). The above-described air permeability of the acquisition layer 70 may advantageously provide improved dryness (e.g., via lower rewet) and reduced fluid intake time relative to acquisition layers with relatively low void volume and lesser air permeability.

Various characteristics of the acquisition layer 70, such as basis weight, fiber size, and bond pattern area, may be selected to provide the desired air permeability for the acquisition layer 70. For example, the basis weight of the acquisition layer 70 may be no less than sixty grams per square meter (60 gsm) and no greater than one hundred grams per square meter (100 gsm), such as no less than sixty-five grams per square meter (65 gsm) and no greater than ninety grams per square meter (90 gsm), such as no less than seventy grams per square meter (70 gsm) and no greater than eighty-five grams per square meter (85 gsm), such as about eighty grams per square meter (80 gsm). An average thickness of the acquisition layer 70, e.g., along the transverse direction 34, may be no less than two and a half millimeters (2.5 mm) and no greater than five millimeters (5 mm), such as about four millimeters (4 mm). As another example, the acquisition layer 70 may include a bonded carded web of fibers (e.g., bound via through-air or adhesive), such as bicomponent polyethylene and polypropylene fibers and/or polyethylene terephthalate fibers. Thus, e.g., the acquisition layer 70 may be a bonded carded non-woven web with bicomponent polyethylene and polypropylene fibers as well as polyethylene terephthalate fibers, e.g., with a basis weight no less than seventy-five grams per square meter (75 gsm) and no greater than eighty-five grams per square meter (85 gsm). As another example, the acquisition layer 70 may include fibers of differing diameters. For instance: diameters of a first portion of the bicomponent polyethylene and polypropylene fibers in the acquisition layer 70 may be no less than one and one-tenths denier per filament (1.1 dpf) and no greater than two and a half denier per filament (2.5 dpf), such as about one and five-tenths denier per filament (1.5 dpf); diameters of a second portion of the bicomponent polyethylene and polypropylene fibers in the acquisition layer 70 may be no less than four denier per filament (4 dpf) and no greater than six and six-tenths denier per filament (6.6 dpf), no less than four and eight-tenths denier per filament (4.8 dpf) and no greater than five and eight-tenths denier per filament (5.8 dpf), such as about five and three-tenths denier per filament (5.3 dpf); and diameters of polyethylene terephthalate fibers in the acquisition layer 70 may be no less than seven and five-tenths denier per filament (7.5 dpf) and no greater than sixteen denier per filament (16 dpf), no less than eight and three-tenths denier per filament (8.3 dpf) and no greater than twelve denier per filament (12 dpf), such as about nine denier per filament (9 dpf). The first portion of the bicomponent polyethylene and polypropylene fibers in the acquisition layer 70 may be present in the acquisition layer 70 at about twenty percent (20%) by weight of the acquisition layer 70, the second portion of the bicomponent polyethylene and polypropylene fibers in the acquisition layer 70 may be present in the acquisition layer 70 at about forty percent (40%) by weight of the acquisition layer 70, and the polyethylene terephthalate fibers may be present in the acquisition layer 70 at about forty percent (40%) by weight of the acquisition layer 70. In some example embodiments, the bicomponent polyethylene and polypropylene fibers in the acquisition layer 70 may be linearly crimped, and the polyethylene terephthalate fibers in the acquisition layer 70 may be helically crimped. It will be understood that the acquisition layer 70 may be formed from fibers with different compositions and/or using different nonwoven techniques in other example embodiments. As noted above, in example embodiments, the bodyside liner 28 may also be embossed to the acquisition layer 70 at the target zone.

As an example, the absorbent body 35 may have a relatively high amount of superabsorbent material. Moreover, the absorbent body 35 may include a matrix of cellulosic fluff and superabsorbent material. The superabsorbent material may be present in the matrix at no less than fifty percent (50%) by weight of the matrix and no greater than eighty percent (80%) by weight of the matrix, such as no less than fifty percent (50%) by weight of the matrix and no greater than seventy-five percent (75%) by weight of the matrix.

As noted above, the properties of the bodyside liner 28, absorbent body 35, and acquisition layer 70 may facilitate fluid flow within the target zone, e.g., and thus advantageously provide desired dryness. Moreover, in example embodiments, a second rewet of the absorbent article 10 may be less than three-tenths of a gram (0.3 g) according to the Rewet Test, which is described in the Test Methods section below. The dryness (indicated by the second rewet value) provided by the absorbent article 10 can be significantly better than conventional absorbent articles. Thus, the absorbent article 10 may be more comfortable to wear relative to the conventional absorbent articles, which do not provide the same degree of dryness.

In example embodiments, fluid may be controlled (e.g., due to the properties of the bodyside liner 28, absorbent body 35, and acquisition layer 70) such that the fluid spreads no more than five millimeters (5 mm) beyond the length of the acquisition layer to provide the rewet of less than or equal to three-tenths of a gram (0.3 g) according to the Rewet Test. In example embodiments, fluid may be controlled (e.g., due to the properties of the bodyside liner 28, absorbent body 35, and acquisition layer 70 and/or due to the absorbent body 35 including at least ten grams (10 g) of superabsorbent material) such that the fluid spreads no more than five millimeters (5 mm) beyond the length of the acquisition layer to provide the rewet of less than or equal to three-tenths of a gram (0.3 g).

Test Methods:

Air Permeability Test:

Air permeability as used herein is tested according to ASTM Test D-737 (current test as of 2022). The test parameters used are twenty square centimeter (20 cm$^2$) head or thirty-eight square centimeter (38 cm$^2$) and one hundred and twenty-five pascal (125 Pa) pressure. The test can be conducted using a TEXTEST FX 3300 air permeability tester available from ATI Corporation. The equipment can provide air permeability values in ft$^3$/min/ft$^2$, which can be converted to m$^3$/h/m$^2$ via multiplication by 18.288.

Rewet Test:

The following test was conducted to determine fluid intake and rewet. This test categorizes the amount of fluid remaining near the surface of the diaper shortly after insult, as well as quantifies the amount of fluid not locked up by superabsorbent under high pressure after a longer wait and multiple insults. For successful usage, the product must both intake fluid quickly through the layers of the absorbent core, in addition to holding on to fluid to ensure that the fluid does not flow back out when subjected to high pressure. The volume of loadings and the rate of fluid delivery are pre-defined based on previous consumer studies with the product. These values can vary from product to product.

Equipment and Supplies for the testing include: (1) a top loading electronic balance capable of reading 0.001 gram; (2) saline solution, 0.9+0.005% (w/w) aqueous isotonic saline; (3) countdown timer, readable to 0.1 second; (4) rectangular plexiglass plate with dimensions of length=300 mm and width=100 mm and including an open cylinder located in a central area of the plate, the internal diameter of the cylinder being 38 mm and the height being 125 mm; (5) two weights of 4 kg each; (6) blotter paper verigood grade, white, 100 lb, 475 by 600 mm (19 by 24 inches) long stock, 250 sheets per ream, cut to a specified size of 88×300 mm+/−13 mm (3 5 by 12 inches); (7) polycarbonate plate (3 675 mm thick) cut to 114 mm wide×432 mm long (4 5 by 17 inches) and weighing 177 grams; (8) funnel polyethylene, 4 ounce capacity; (9) low tack two-sided tape or attachment material to secure product flat on surface; (10) stopwatch, readable to 0.1 second; and (11) ruler.

Sample Preparation for the testing is as follows. Based on the product size determine insult size and rate from table below.

For the testing, first, place the product on a flat plane and fix the top and bottom ends to the two-sided tape so that the product is stretched and the absorbent core lays flat. Second, place the board with open cylinder on the stretched product so that the top edge of the plate is aligned with the edge of the absorbent core. Put the funnel in the top of the open cylinder in the plate. Third, weigh one sheet of blotter paper on the balance readable to three decimal places. Record the weight of the paper. Fourth, pour the specified quantity of saline solution into the funnel in accordance with the size of the product being tested by following the instructions in the table below. Simultaneously activate the stopwatch. Fifth, stop the stopwatch as soon as the liquid passes completely from the cylinder and into the product (no liquid being on the surface of the product). Start the timer set to 30 seconds and the timer set to 15 minutes. Sixth, record the intake time. Seventh, after waiting 30 seconds, remove the plate with the open cylinder. Place the pre-weighed blotter paper on the product and place the polycarbonate board on top of the product. Eighth, start the timer set to 2 minutes. Nineth, after waiting 2 minutes, remove the polycarbonate board and blotter paper. Place the plate with the open cylinder on the product again and leave on the product for the duration of the wait. Tenth, weigh the blotter paper to the nearest thousandth, and record the weight. Eleventh, mark the two ends down the length of the blotter paper that the fluid extends to. Measure that distance in centimeters lengthwise down the blotter paper and widthwise. Multiply those two distances together to get the area (spread) of the fluid. Record spread. Twelfth, after the 15 minute wait, place the one weight on both sides of the cylinder on the board. Pour the specified quantity of saline solution, depending on the table below, into the funnel placed in the cylinder. Simultaneously start the stopwatch and start the countdown timer set to 15 minutes. Thirteenth, stop the stopwatch as soon as the liquid passes completely through the cylinder and into the product (no liquid being on the surface of the product). Record the second intake time. Leave the plate with the open cylinder and weights on the product for the duration of wait time. Fourteenth, weigh two sheets of blotter paper, and record the weight to three decimal places. Fifteenth, after the 15 minute wait, remove the weights and rectangular board with cylinder. Place the preweighed blotter paper onto the product, and then place the polycarbonate board and the two weights on top of that. Start the timer set for 2 minutes. Sixteenth, after the 2 minute wait, remove the weights,

| | | | | Product Size | | | | | |
|---|---|---|---|---|---|---|---|---|---|
| | N | Step 1 | Step 2 | Step 3 | Step 4 | Step 5 | 2 T/3 T | 3 T/4 T | 4 T/5 T |
| Rate (ml/s) | 9 | 10 | 12 | 15 | 15 | 15 | 15 | 15 | 15 |
| Volume (ml) | 40 | 50 | 60 | 70 | 85 | 100 | 80 | 100 | 110 |
| Target Location (cm) (measured from center) | 4 | 5.5 | 6.5 | 7.5 | 8.5 | 9.5 | 8.5 | 9 | 9.5 |

Next, weigh product to the nearest 0.01 grams and record, discard specimens out of weight range determined by requestor if applicable.

For the testing setup, ensure saline is at room temperature, have three countdown timers set for 30 seconds, 2 minutes, and 15 minutes.

polycarbonate board, and blotter paper. Immediately weigh the blotter paper on a scale readable to three decimal places and record the weight. Seventeenth, mark the two ends down the length of the blotter paper that the fluid extends to. Measure that distance in centimeters lengthwise down the blotter paper and widthwise. Multiply those two distances together to get the area (spread) of the fluid. Record spread. Eighteenth, remove the product from the surface. Weigh the product and record the weight.

Shake Test:

A suitable apparatus and procedure for determining the shake-out value of a sample material is described in PCT publication WO 02/076520 published Oct. 3, 2002, which is incorporated in its entirety herein for all purposes. The susceptibility of an absorbent article with a superabsorbent/ fiber web to the migration and escape of superabsorbent material (SAM) can be measured by employing a shake test procedure, which involves agitating samples in a controlled fashion and determining the total loss of mass from the sample.

The Shake Test can be conducted by employing a Model #RX-24 PORTABLE SIEVE SHAKER (herein after referred to as "RX-24") available from W. S. Tyler Inc. (having a place of business in Mentor, Ohio, U.S.A.). The shaker apparatus is modified in the manner described in PCT publication WO 02/076520. For use in the Shake Test, the RX-24 is modified to shake samples and allow a determination of the sample's resistance to the migration of superabsorbent material (SAM), based on the mass loss of sample during the shaking. The modifications to the shaker apparatus involve making changes to the guide frame in the manner described in PCT publication WO 02/076520. In addition to the changes to the guide frame described in this PCT publication, a modified sample holder is employed in the shakeout test. The sample holder has a frame made of polyacrylate plate and two pieces of mesh screen. The frame has a length of 17 inches (43.18 cm), a width of 11.5 inches (29.21 cm) and a thickness of 0.20 inch (0.51 cm). The frame has a rectangular opening with a length of 15.25 inches (38.74 cm) and a width of 6.25 inches (15.88 cm), and the opening is substantially centered in the frame. One piece of mesh screen with a dimension slightly larger than the opening is operatively joined on each side of the frame (e.g., with duct tape) to hold the test sample. The mesh screen has 0.4 cm×0.4 cm square openings, and the total weight of the sample holder is about 500 grams. A substantially equivalent shaker system may optionally be employed.

To perform the Shake Test, the sample is laid at the center of the sample holder, and the sample holder is laid horizontally flat (i.e. parallel to the floor) upon the wire screen employed to support the sample on the modified RX-24. The RX-24 then shakes the web at a frequency of 520 cycles per minute for a period of five minutes. If any sheets of tissue paper or other material have been placed above or below the sample to facilitate the lifting or handling of the web samples, those sheets are removed prior to shaking.

After the completion of the shaking portion of the test, the mass loss and the superabsorbent-loss are determined by comparing the total remaining mass of the absorbent composite sample with the original mass of the sample when the sample was initially placed on the support screen, in accordance with the following formula:

$$\text{Mass loss (\%)} = 100\% \times ((M_0 - M_{end}) \div M_0)$$

where: $M_0$=sample mass prior to shake test (e.g. grams);
$M_{end}$=sample mass remaining after test (e.g. grams).

Mass that is lost from the sample will generally fall through the openings in the support screen. Any mass that remains on the screen is counted as mass loss. The superabsorbent shakeout value (%) is the total mass loss (%) produced at the above-described shaking conditions.

While the foregoing discussion has described in detail one desirable method for conducting the Shake Test using a specific type of apparatus, it will be appreciated that those skilled in the art will be able to prepare other apparatus that will allow equivalent testing in which agitation applied to samples will yield the identical results in terms of mass loss as that achieved by the disclosed Shake Test. Accordingly, the scope of the Shake Test will include any equivalent test methods for determining mass loss.

EXAMPLES

Absorbent articles were made from various bodyside liners and acquisition layers. The absorbent core of each article included a matrix of cellulosic fluff and superabsorbent material with superabsorbent material present in the matrix at about sixty percent (60%) by weight of the matrix. The superabsorbent material generally consists of a partially neutralized lightly cross-linked polymer network, namely polyacrylate, which is hydrophilic and permits swelling of the network.

The composition of the bodyside liners and acquisition layers is summarized in Table 1 below.

TABLE 1

| | Bodyside Liner Composition | Acquisition Layer Composition |
|---|---|---|
| Sample 1 | 1.6 dpf PP @ 12 gsm | 40% 9 dpf PET, 60% 5.3 dpf PE/PP @ 80 gsm |
| Sample 2 | 1.6 dpf PP @ 12 gsm | 40% 9 dpf PET, 60% 5.3 dpf PE/PP @ 80 gsm |
| Sample 3 | Commercially available liner from Snug & Dry diaper @ 12 gsm | 40% 9 dpf PET, 60% 5.3 dpf PE/PP @ 80 gsm |
| Sample 4 | Commercially available liner from Little Movers diaper @ 20 gsm | 40% 9 dpf PET, 60% 5.3 dpf PE/PP @ 80 gsm |
| Sample 5 | Commercially available liner from Snug & Dry diaper @ 12 gsm | 30% 6 dpf PET, 35% 5.3 dpf PE/PP 35% 1.5 dpf PE/PP @ 100 gsm, |
| Sample 6 | Commercially available liner from Little Movers diaper @ 20 gsm | 30% 6 dpf PET, 35% 5.3 dpf PE/PP, 35% 1.5 dpf PE/PP @ 100 gsm |

The bodyside liner of Sample 1 was untreated. The bodyside liner of Sample 2 was treated with surfactant blend to adjust wettability. The surfactant formulation included a blend of hydrogenated ethoxylated castor oil and sorbitan monooleate from Croda along with a proprietary surfactant commercially available from Schill & Seilacher AG and a proprietary surfactant commercially available from Pulcra Chemical LLC. The bodyside liner of Sample 2 was treated with a reduced level of surfactant, for example 0.35% when 0.45% or higher levels are typically used. The air permeability values of the bodyside liners and acquisition layers are provided below in Table 2. The bodyside liners of Sample 3 through 6 were treated with a typical level of surfactant.

TABLE 2

|  | Bodyside Liner Air Permeability | Acquisition Layer Air Permeability |
|---|---|---|
| Sample 1 | $18{,}032 \pm 914$ m³ph/m² | $15800 \pm 439$ m³ph/m² |
| Sample 2 | $18{,}745 \pm 1042$ m³ph/m² | $15800 \pm 439$ m³ph/m² |
| Sample 3 | $11{,}192 \pm 640$ m³ph/m² | $15800 \pm 439$ m³ph/m² |
| Sample 4 | $12{,}728 \pm 238$ m³ph/m² | $15800 \pm 439$ m³ph/m² |
| Sample 5 | $11{,}192 \pm 640$ m³ph/m² | $9254 \pm 421$ m³ph/m² |
| Sample 6 | $12{,}728 \pm 238$ m³ph/m² | $9254 \pm 421$ m³ph/m² |

The second rewet values of the absorbent articles are provided below in Table 3.

TABLE 3

|  | Second Rewet |
|---|---|
| Sample 1 | $0.26 \pm 0.04$ g |
| Sample 2 | $0.28 \pm 0.06$ g |
| Sample 3 | $0.82 \pm 0.39$ g |
| Sample 4 | $0.46 \pm 0.11$ g |
| Sample 5 | $2.96 \pm 1.25$ g |
| Sample 6 | $1.42 \pm 0.76$ g |

As may be seen from the above, Samples 1 and 2 achieved the second rewet target of ≤0.3 gram and offer significantly better dryness than the other samples.

Additional testing was performed to evaluate differing concentrations of superabsorbent material within the absorbent core of samples. The composition of the bodyside liners, acquisition layers, and absorbent core is summarized in Table 4 below.

TABLE 4

|  | Bodyside Liner Composition | Acquisition Layer Composition | Absorbent Core Composition |
|---|---|---|---|
| Sample 7 | 12 gsm dSB PP | 20% 1.5 dpf PE/PP, 40% 5.3 dpf PE/PP, 40% 9 dpf PET @ 80 gsm | 10.89 g SAM/11.62 g Fluff |
| Sample 8 | 12 gsm dSB PP | 20% 1.5 dpf PE/PP, 40% 5.3 dpf PE/PP, 40% 9 dpf PET @ 80 gsm | 8.73 g SAM/10.55 g Fluff |
| Sample 9 | 14 gsm SB PP | 20% 1.5 dpf PE/PP, 40% 5.3 dpf PE/PP, 40% 9 dpf PET @ 80 gsm | 12.16 g SAM/10.67 g Fluff |
| Sample 10 | 14 gsm SB PP | 20% 1.5 dpf PE/PP, 40% 5.3 dpf PE/PP, 40% 9 dpf PET @ 80 gsm | 8.86 g SAM/10.35 g Fluff |

The second rewet values of the absorbent articles are provided below in Table 5, which also include fluid stain length values measured after the Rewet Test was completed.

TABLE 5

|  | Second Rewet | Fluid Stain Length |
|---|---|---|
| Sample 7 | 0.49 g (3H) | 2.9 mm |
| Sample 8 | 0.94 g (3L) | 6.2 mm |
| Sample 9 | 0.33 g (10H) | 4.4 mm |
| Sample 10 | 0.76 g (10L) | 7.3 mm |

The fluid stain lengths were measured by recording the length of the fluid stain that went beyond the length of the acquisition layer in the Samples.

As may be seen from the above, Sample 9 achieved the second rewet target of about 0.3 gram and offers significantly better dryness than the other samples. In both of the samples with higher weights of superabsorbent material, Samples 7 and 9, less liquid spread beyond the length of the acquisition layer. In contrast, in both of the samples with lower weights of superabsorbent material, Samples 8 and 10, more liquid transferred to portions of the absorbent core not covered by the acquisition layer. Therefore, Samples 7 and 9 with more superabsorbent were able to control the fluid more effectively, which resulted in lower rewet.

Additional testing was performed to evaluate migration and escape of the superabsorbent material from samples. Absorbent articles were made from various bodyside liners and acquisition layers. The absorbent core of each article included a matrix of cellulosic fluff and superabsorbent material with superabsorbent material present in the matrix at about sixty percent (60%) by weight of the matrix. The composition of the bodyside liners and acquisition layers is summarized in Table 6 below.

TABLE 6

|  | Bodyside Liner Composition | Acquisition Layer Composition |
|---|---|---|
| Sample 11 | 12 gsm dSB PP | 20% 1.5 dpf PE/PP, 40% 5.3 dpf PE/PP, 40% 9 dpf PET @ 80 gsm |
| Sample 12 | 12 gsm SB PP | 20% 1.5 dpf PE/PP, 40% 5.3 dpf PE/PP, 40% 9 dpf PET @ 80 gsm |
| Sample 13 | 15 gsm SB PP | 20% 1.5 dpf PE/PP, 40% 5.3 dpf PE/PP, 40% 9 dpf PET @ 80 gsm |
| Sample 14 | 14 gsm SB PP | 20% 1.5 dpf PE/PP, 40% 5.3 dpf PE/PP, 40% 9 dpf PET @ 80 gsm |
| Sample 15 | Commercially available liner from Snug & Dry diaper @ 12 gsm | 30% 6 dpf PET, 35% 5.3 dpf PE/PP, 35% 1.5 dpf PE/PP @ 100 gsm |
| Sample 16 | 12 gsm SB PP | 40% 9 dpf PET, 60% 5.3 dpf PE/PP @ 80 gsm |

The bodyside liner of Samples 11 and 15 was treated with the typical level of surfactant. The bodyside liner of Samples 12, 13, 14, and 16 were semi-treated with a reduced level of surfactant blend to adjust wettability, for example 0.35% when 0.45% or higher levels are typically used. For bodyside liners of Samples 12 and 16, the surfactant formulation included a blend of hydrogenated ethoxylated castor oil and sorbitan monooleate from Croda along with a proprietary surfactant commercially available from Schill & Seilacher AG and a proprietary surfactant commercially available from Pulcra Chemical LLC. For Samples 13 and 14, the surfactant formulation included a blend of hydrogenated ethoxylated castor oil and sorbitan monooleate from Croda along with a proprietary surfactant commercially available from Schill & Seilacher AG. The air permeability values of the bodyside liners and the results of the Shake Tests are provided below in Table 7.

TABLE 7

|  | Bodyside Liner Air Permeability | SAM Shake (particle count) |
| --- | --- | --- |
| Sample 11 | 11,997 m³ph/m² | 7.7 g |
| Sample 12 | 17227 m³ph/m² | 52.7 g |
| Sample 13 | 13972 m³ph/m² | 9.6 g |
| Sample 14 | 15673 m³ph/m² | 6.2 g |
| Sample 15 | 10150 m³ph/m² | 7.6 g |
| Sample 16 | 18800 m³ph/m² | 49.6 g |

As may be seen from the above, Samples 12 and 16 had relatively high SAM Shake Test numbers, which can indicate undesirable SAM migration and escape. Conversely, Samples 11, 13, 14, and 15 had relatively low SAM Shake Test numbers, which can indicate desirable SAM retention within the absorbent article. In general, bodyside liners with higher basis weights had lower SAM Shake Test numbers and lower air permeability, which as noted above can negatively affect the second rewet values. Of particular note, Sample 14 includes a bodyside liner with low SAM Shake particle count and with high air permeability, which reduces rewet.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

Example Embodiments

First example embodiment: An absorbent article, comprising: a bodyside liner having an air permeability no less than thirteen thousand cubic meters per hour per square meter surface and no greater than sixteen thousand, five hundred cubic meters per hour per square meter surface; an absorbent core comprising a matrix of cellulosic fluff and superabsorbent material, the superabsorbent material present in the matrix at no less than fifty percent by weight of the matrix and no greater than eighty percent by weight of the matrix; and an acquisition layer positioned between the bodyside liner and the absorbent core, the acquisition layer having an air permeability no less than twelve thousand, seven hundred cubic meters per hour per square meter surface.

Second example embodiment: The absorbent article of the first example embodiment, wherein a basis weight of the bodyside liner is no less than ten grams per square meter and no greater than twenty grams per square meter.

Third example embodiment: The absorbent article of either the first example embodiment or the second example embodiment, wherein the bodyside liner comprises a nonwoven web of surfactant treated hydrophilic fibers.

Fourth example embodiment: The absorbent article of any one of the first through third example embodiments, wherein the basis weight of the bodyside liner is about twelve grams per square meter.

Fifth example embodiment: The absorbent article of any one of the first through fourth example embodiments, wherein the acquisition layer comprises a nonwoven web of helically crimped fibers and linearly crimped fibers.

Sixth example embodiment: The absorbent article of any one of the first through fifth example embodiments, wherein the helically crimped fibers and the linearly crimped fibers are formed from different polymers.

Seventh example embodiment: The absorbent article of any one of the first through sixth example embodiments, wherein a basis weight of the acquisition layer is no less than sixty grams per square meter and no greater than one hundred grams per square meter.

Eighth example embodiment: The absorbent article of any one of the first through seventh example embodiments, wherein a second rewet of the absorbent article is less than or equal to three-tenths of a gram according to a Rewet Test.

Nineth example embodiment: The absorbent article of any one of the first through eighth example embodiments, wherein fluid spreads no more than five millimeters beyond a length of the acquisition layer to provide rewet of less than or equal to three-tenths of a gram according to a Rewet Test.

Tenth example embodiment: The absorbent article of any one of the first through nineth example embodiments, wherein the absorbent core contains at least ten grams of superabsorbent material, and fluid spreads no more than five millimeters beyond a length of the acquisition layer to provide rewet of less than or equal to three-tenths of a gram according to a Rewet Test.

Eleventh example embodiment: The absorbent article of any one of the first through tenth example embodiments, wherein the bodyside liner is embossed to the acquisition layer.

Twelfth example embodiment: The absorbent article of any one of the first through eleventh example embodiments, wherein: each of the bodyside liner, the absorbent core, and the acquisition layer has a respective length along a longitudinal direction of the absorbent article; and the length of the acquisition layer is less than the lengths of the bodyside liner and the absorbent core.

Thirteenth example embodiment: An absorbent article, comprising: a bodyside liner having an air permeability no less than thirteen thousand cubic meters per hour per square meter surface and no greater than sixteen thousand, five hundred cubic meters per hour per square meter surface, a basis weight of the bodyside liner being no less than ten grams per square meter and no greater than twenty grams per square meter; an absorbent core comprising a matrix of cellulosic fluff and superabsorbent material, the superabsorbent material present in the matrix at no less than fifty percent by weight of the matrix and no greater than eighty percent by weight of the matrix; and an acquisition layer positioned between the bodyside liner and the absorbent core, the acquisition layer having an air permeability no less than twelve thousand, seven hundred cubic meters per hour per square meter surface, a basis weight of the acquisition layer being no less than sixty grams per square meter and no greater than one hundred grams per square meter.

Fourteenth example embodiment: The method of the thirteenth example embodiment, wherein the bodyside liner comprises a nonwoven web of surfactant treated hydrophilic fibers.

Fifteenth example embodiment: The method of either the thirteenth example embodiment or the fourteenth example embodiment, wherein the basis weight of the bodyside liner is about twelve grams per square meter.

Sixteenth example embodiment: The method of any one of the thirteenth through fifteenth example embodiments, wherein the acquisition layer comprises a nonwoven web of helically crimped fibers and linearly crimped fibers.

Seventeenth example embodiment: The method of any one of the thirteenth through sixteenth example embodiments, wherein the helically crimped fibers and the linearly crimped fibers are formed from different polymers.

Eighteenth example embodiment: The method of one of the thirteenth through seventeenth example embodiments, wherein a second rewet of the absorbent article is less than or equal to three-tenths of a gram according to a Rewet Test.

Nineteenth example embodiment: The method of one of the thirteenth through eighteenth example embodiments, wherein the bodyside liner is embossed to the acquisition layer.

Twentieth example embodiment: The method of one of the thirteenth through nineteenth example embodiments, wherein: each of the bodyside liner, the absorbent core, and the acquisition layer has a respective length along a longitudinal direction of the absorbent article; and the length of the acquisition layer is less than the lengths of the bodyside liner and the absorbent core.

What is claimed:

1. An absorbent article, comprising:
a bodyside liner having an air permeability no less than thirteen thousand cubic meters per hour per square meter surface and no greater than sixteen thousand, five hundred cubic meters per hour per square meter surface, wherein the bodyside liner comprises a nonwoven web of surfactant treated hydrophilic fibers;
an absorbent core comprising a matrix of cellulosic fluff and superabsorbent material, the superabsorbent material present in the matrix at no less than fifty percent by weight of the matrix and no greater than eighty percent by weight of the matrix; and
an acquisition layer positioned between the bodyside liner and the absorbent core, the acquisition layer having an air permeability no less than twelve thousand, seven hundred cubic meters per hour per square meter surface.

2. The absorbent article of claim 1, wherein a basis weight of the bodyside liner is no less than ten grams per square meter and no greater than twenty grams per square meter.

3. The absorbent article of claim 1, wherein the basis weight of the bodyside liner is about twelve grams per square meter.

4. The absorbent article of claim 1, wherein the acquisition layer comprises a nonwoven web of helically crimped fibers and linearly crimped fibers.

5. The absorbent article of claim 4, wherein the helically crimped fibers and the linearly crimped fibers are formed from different polymers.

6. The absorbent article of claim 1, wherein a basis weight of the acquisition layer is no less than sixty grams per square meter and no greater than one hundred grams per square meter.

7. The absorbent article of claim 1, wherein a second rewet of the absorbent article is less than or equal to three-tenths of a gram according to a Rewet Test.

8. The absorbent article of claim 1, wherein fluid spreads no more than five millimeters beyond a length of the acquisition layer to provide rewet of less than or equal to three-tenths of a gram according to a Rewet Test.

9. The absorbent article of claim 1, wherein the absorbent core contains at least ten grams of superabsorbent material, and fluid spreads no more than five millimeters beyond a length of the acquisition layer to provide rewet of less than or equal to three-tenths of a gram according to a Rewet Test.

10. The absorbent article of claim 1, wherein the bodyside liner is embossed to the acquisition layer.

11. The absorbent article of claim 1, wherein:
each of the bodyside liner, the absorbent core, and the acquisition layer has a respective length along a longitudinal direction of the absorbent article; and
the length of the acquisition layer is less than the lengths of the bodyside liner and the absorbent core.

12. An absorbent article, comprising:
a bodyside liner having an air permeability no less than thirteen thousand cubic meters per hour per square meter surface and no greater than sixteen thousand, five hundred cubic meters per hour per square meter surface, a basis weight of the bodyside liner being no less than ten grams per square meter and no greater than twenty grams per square meter, wherein the bodyside liner comprises a nonwoven web of surfactant treated hydrophilic fibers;
an absorbent core comprising a matrix of cellulosic fluff and superabsorbent material, the superabsorbent material present in the matrix at no less than fifty percent by weight of the matrix and no greater than eighty percent by weight of the matrix; and
an acquisition layer positioned between the bodyside liner and the absorbent core, the acquisition layer having an air permeability no less than twelve thousand, seven hundred cubic meters per hour per square meter surface, a basis weight of the acquisition layer being no less than sixty grams per square meter and no greater than one hundred grams per square meter.

13. The absorbent article of claim 12, wherein the basis weight of the bodyside liner is about twelve grams per square meter.

14. The absorbent article of claim 12, wherein the acquisition layer comprises a nonwoven web of helically crimped fibers and linearly crimped fibers.

15. The absorbent article of claim 14, wherein the helically crimped fibers and the linearly crimped fibers are formed from different polymers.

16. The absorbent article of claim 12, wherein a second rewet of the absorbent article is less than or equal to three-tenths of a gram according to a Rewet Test.

17. The absorbent article of claim 12, wherein the bodyside liner is embossed to the acquisition layer.

18. The absorbent article of claim 12, wherein:
each of the bodyside liner, the absorbent core, and the acquisition layer has a respective length along a longitudinal direction of the absorbent article; and
the length of the acquisition layer is less than the lengths of the bodyside liner and the absorbent core.

19. The absorbent article of claim 1, wherein the superabsorbent material is present in the matrix at no less than fifty percent by weight of the matrix and no greater than seventy-five percent by weight of the matrix.

20. The absorbent article of claim 1, wherein a surfactant may be applied to the bodyside liner to provide an add-on no less than two-tenths percent and no greater than one percent.

* * * * *